United States Patent [19]

Founds, Jr. et al.

[11] Patent Number: 4,794,076

[45] Date of Patent: Dec. 27, 1988

[54] SIMULTANEOUS EXTRACTION OF A LIGAND FROM A SAMPLE AND CAPTURE BY ANTI-LIGANDS THEREFOR IN LIGAND/ANTI-LIGAND ASSAYS

[75] Inventors: Henry W. Founds, Jr., Scarboro; Roger N. Piasio, Yarmouth, both of Me.

[73] Assignee: VXR, Inc., Portland, Me.

[21] Appl. No.: 779,212

[22] Filed: Sep. 23, 1985

[51] Int. Cl.$^4$ .............. G01N 33/535; G01N 33/545; G01N 33/569

[52] U.S. Cl. ........................ 435/7; 436/518; 436/530; 436/531; 436/804

[58] Field of Search ............ 435/7; 436/518, 530, 436/531, 804

[56] References Cited

U.S. PATENT DOCUMENTS

| | | | |
|---|---|---|---|
| Re. 29,169 | 4/1977 | Schuurs | 435/7 |
| 4,503,143 | 3/1985 | Gerber | 435/7 |
| 4,618,576 | 10/1986 | Rosenstein | 435/36 X |

OTHER PUBLICATIONS

Ross, P. W. et al., J. Clin. Pathol., 33, 691–693, (1980).
Kaplan, L. E., et al., J. Clin. Micro., 14 (6):678–680, 1981.
Cumming, C. G. et al., J. Med. Micro., 13:459–461, 1980.
Facklam, R. R. et al., J. Clin. Micro., 15 (6), 987–990, 1982.

*Primary Examiner*—Sidney Marantz
*Attorney, Agent, or Firm*—David G. Conlin; Linda M. Buckley

[57] ABSTRACT

Methods and kits for performing a ligand/anti-ligand assay are described. The ligand/anti-ligand assay comprises: (1) simultaneously carrying out the extraction of a ligand from a sample of cells or cells and reaction of the ligand with at least two anti-ligands therefor to form a detectable reaction product, and (2) detecting the reaction product.

28 Claims, 1 Drawing Sheet

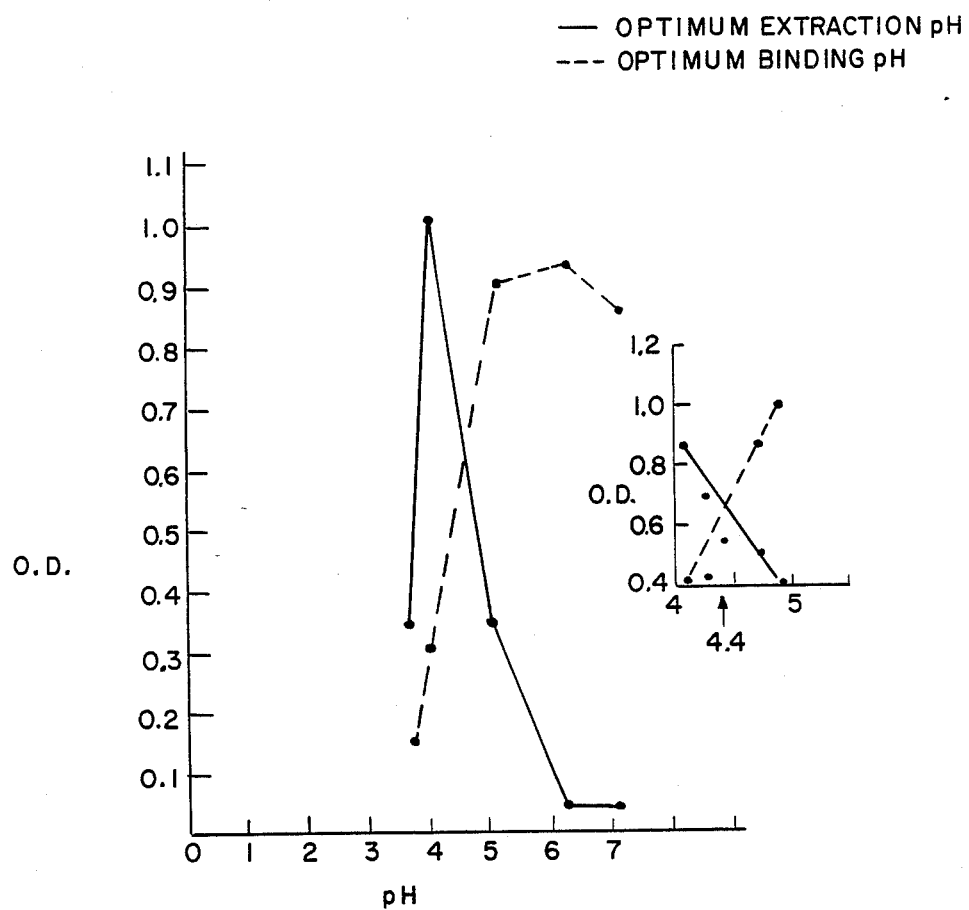
FIG. I

SIMULTANEOUS EXTRACTION OF A LIGAND FROM A SAMPLE AND CAPTURE BY ANTI-LIGANDS THEREFOR IN LIGAND/ANTI-LIGAND ASSAYS

FIELD OF THE INVENTION

This invention relates to assays of ligands extracted from a sample of cells or cell fragments by (1) simultaneously carrying out the extraction of a ligand from the sample and reaction of the ligand with at least two anti-ligands therefor to form a reaction product; and (2) detecting the reaction product. This invention further relates to methods of carrying out such assays and kits comprising ingredients to practice such methods.

BACKGROUND OF THE INVENTION

Techniques for assaying a liquid sample for the presence and/or concentration of specific substances are known to those skilled in the art. Examples of such techniques include radioimmunoassays (RIA), enzyme immunoassays (EIA), enzyme-linked immunoassays (ELISA), and related protein-binding methodologies. All of these techniques involve the binding of a compound to some sort of specific receptor and accordingly fall into the general category of ligand/anti-ligand assays, a category not limited to any special type of interaction occurring in the assay or to any particular type of components participating in the reaction. All ligand/anti-ligand assays are based on two premises: (1) that certain pairs of substances (the ligand and the anti-ligand) have a strong and specific affinity for each other, that is, they will tend to bind to each other, while binding little or not at all to other substances; and (2) that methods can be developed that allow detection of ligand/anti-ligand binding interactions once complexes have formed. As used herein, ligand is defined as the substance to be detected, and anti-ligand the substance used to probe for the presence of the ligand. In some ligand/anti-ligand assays, an additional, perhaps modified, ligand may be used that competes with the substance to be detected for binding sites on the anti-ligand. Immobilization of either the ligand or anti-ligand will in some cases facilitate detection of the reaction product.

Ligand/anti-ligand reactions can be detected by a variety of methods using various markers to label the reaction product. Currently, the most commonly used markers include enzymes and fluorochromes and radioactive compounds.

Ligand/anti-ligand assay methods can be applied to enzyme immunoassays to detect the presence or absence of antibodies or antigens, i.e., ligands in a sample. In recent years, the use of EIAs and ELISAs has become increasingly important for the detection and quantitation of biologically active substances. In typical ELISA methodology, antigens can be detected directly or indirectly by capture of the antigen with a specific antibody and detection of the bound antigen by use of enzyme-labeled antibodies which catalyze, under appropriate conditions, a reaction with a substrate. The enzyme activity is generally detected by formation of a colored reaction product. Several enzymes, including alkaline phosphatase, horseradish peroxidase and glucose oxidase have been coupled to antigen or antibody. Horseradish peroxidase (HRP) is commonly used. Several substrates are available for (HRP). For visual detection, the substrate will usually comprise a solution of hydrogen peroxide and a chromogenic material, such as, o-phenylenediamine or tetramethylbenzidine, which manifests a color upon oxidation.

In fluorescent immunoassay techniques (FIA) antigens can be labeled directly or indirectly with fluorochrome-labeled antibodies. Fluorochromes are dyes that absorb radiation (e.g., ultraviolet light), are excited by it, and emit light (e.g., visible light). The most commonly used fluorochromes are fluorescein isothiocyante and tetramethylrhodamine isothiocyanate.

The detection via ligand/anti-ligand reactions of analytes in a biological sample has been achieved through the use of methods employing radioactively labeled compounds. Various RIA techniques, for the direct or indirect measurement of ligands, are well known to those skilled in the art.

Ligand/anti-ligand assays have applications in the field of medicine, for example, in the diagnosis of infectious diseases. Accurate diagnosis and treatment of infection is possible only after the exact identity of the etiological agent has been established. In the case of microorganisms, species or group specific antigens, i.e., ligands, which may be used to identify the microorganism and/or to further identify its group, can be extracted from, e.g., the whole cell, the cell wall, or cell fragments. It is desirable that assays for the detection of such ligands be simple and fast.

Group A Streptococcal antigen, a polysaccharide, can be advantageously assayed by use of ligand/anti-ligand assays. Beta-hemolytic, pathogenic Group A streptococci are the most common bacterial agent associated with infections of the upper respiratory tract and of the skin in humans. The highest occurrence is typically found in children. Antibiotic therapy is the treatment of choice. If left untreated, a Group A streptococcal infection may lead to more serious complications such as rheumatic fever (Wannamaker, L. E.: *Reviews of Inf. Dis.*, 1:967–973, 1979; Catanzaro, F. J., et al.: *Amer. J. Med.*, 17:749–756, 1954). Because of the high frequency of Group A Streptococci as etiological agents of human disease, simple and fast methods of diagnosis are being sought.

Methods currently used to identify Group A streptococci isolated from culture include bacitracin susceptibility and latex slide agglutination. Confirmatory methods include immunofluorescence, precipitin tests and coagglutination (Kaplan, L. K., et al., *J. Clin. Micro.*, 14 (6):678–680, 1981; Ross, P. W. et al.: *J. Clin. Pathol.*, 33:691–693, 1980; Cumming, C. G. et al., *J. Med. Micro.*, 13:459–461, 1980; Facklam, R. R. et al., *J. Clin. Micro.*, 15(6):987–990, 1982; Fung, J. et al., *Am. J. Clin. Path.*, 5:608–610, 1982; and Edwards, E. A. et al., *J. Clin. Micro.*, 15(3): 481–483, 1982).

Extraction of group-specific polysaccharides from the cell wall of streptococci is achieved with extraction reagents comprising an acid. The art teaches neutralization of acid extracted Group A Streptococcal antigen before carrying out an immunological assay procedure to detect the presence of the antigen. The neutralization step increases the time it takes to carry out such assays. It would therefore be advantageous to have an assay for acid extracted Group A Streptococcal antigen which is simpler and more rapid than those known in the art.

It would further be advantageous to have assay procedures for ligands extracted from cells or cell fragments which permit simultaneously carrying out the extraction of the ligand from the sample and reaction of the ligand with at least two anti-ligands therefor to form a detectable reaction product.

SUMMARY OF THE INVENTION

The present invention provides, among other things, methods for detecting ligands extracted from a sample of cells or cell fragments and kits comprising ingredients to practice such methods. Methods, according to the present invention, are relatively rapid and simple due to simultaneous extraction of the ligand from the sample and reaction of the ligand with at least two anti-ligands therefor. Accordingly, the present invention provides a method for performing an assay of a ligand extracted from a sample of cells or cell fragments, the method comprising: (1) simultaneously carrying out the extraction of the ligand from the sample and reaction of the ligand with at least two anti-ligands therefor to form a detectable reaction product; and (2) detecting the reaction product.

In some embodiments the present invention further provides solid phase ligand/anti-ligand assays wherein at least one anti-ligand is immobilized in or on a solid support.

In one embodiment, the present invention provides an immunoassay method for performing an assay of acid extracted Group A Streptococcal antigen, the method comprising: (1) simultaneously carrying out the acid or enzyme extraction of Group A Streptococcal antigen from a sample of cells or cell fragments and reaction of the antigen with a first and second antibody therefor to form a detectable reaction product; and (2) detecting the reaction product.

The present invention also provides a kit for performing the assay of a ligand extracted from a sample of cell or cell fragments, the assay comprising: (1) simultaneously carrying out the extraction of the ligand from the sample and reaction of the ligand with at least two anti-ligands therefor to form a detectable reaction product, and (2) detecting the reaction product; the kit comprising, in combination: one or more solutions comprising an extraction reagent for the ligand and at least two anti-ligands therefor, one anti-ligand having a label capable of detection. In one embodiment the present invention provides a kit for carrying out immunoassays, the kit comprising, in combination:
1. at least one solution comprising an extraction reagent for an antigen;
2. an immobilized first antibody for the antigen;
3. a second antibody for the antigen conjugated with an enzyme; and
4. a substrate for the enzyme; and
5. a chromogen.

BRIEF DESCRIPTION OF THE DRAWINGS

FIG. 1 is a graph illustrating the results obtained in immunoassays to determine the optimum pH for simultaneous extraction and immunochemical binding of Group A Streptococcal antigen.

DETAILED DESCRIPTION OF THE INVENTION

In accord with the present invention, a method for the assay of a ligand extracted from a sample of cells or cell fragments is provided. The method comprises (1) simultaneously carrying out the extraction of a ligand from a sample and reaction of or more anti-ligands with the ligand to form a detectable reaction product; and (2) detecting the reaction product. In some embodiments of the present invention the method further comprises a wash step before the detection step. In yet other embodiments the sample is absorbed in or adsorbed on a matrix.

Methods in accordance with the present invention are particularly suited to solid phase ligand/anti-ligand assays. Accordingly, the present invention further provides a method for performing the assay of a ligand extracted from a sample of cells or cell fragments, the method comprising: (1) absorbing in or adsorbing on a matrix a sample containing the ligand; (2) placing the matrix, before or after absorption or adsorption of the sample, in a container, the container being coated with or containing an immobilized substance comprising a first anti-ligand for the ligand; (3) carrying out the simultaneous extraction of the ligand and reaction of the ligand with at least two anti-ligands therefor to form a detectable reaction product by (i) adding to the container, one or more extraction reagents in an amount to extract at least a portion of the ligand sufficient to form a quantity of reaction product capable of detection and adding to the container a solution comprising a second anti-ligand for the ligand, the second anti-ligand having a detectable label, and (ii) incubating the contents of the tube for a predetermined period of time to permit extraction of the ligand from the sample and formation of the reaction product; and (4) detecting the reaction product.

In some embodiments of the present invention, the extraction reagent is added to and essentially absorbed in the matrix; a solution of the second anti-ligand is added to the bottom of the container and the ligand, as it is extracted from the sample, diffuses into the second anti-ligand solution and is captured by the first and second anti-ligand. In other embodiments the extraction reagent and second anti-ligand are added consecutively or simultaneously.

Although methods according to the present invention are suitable for any ligand/anti-ligand assay, antigen-/antibody assays are preferred.

The present invention is applicable to any ligand that can be extracted from a sample of cells or cell fragments. Exemplary classes of ligands include, for example, carbohydrates, proteins, peptides, nucleotides, and mixed molecules, e.g., peptides, carbohydrates. Group A Streptococcal antigen is an example of a carbohydrate antigen. The amount of ligand extracted can vary over a wide range as long as there is sufficient ligand so that the ligand/anti-ligand reaction product is capable of detection either by an appropriate instrument or visually.

In some embodiments of the present invention, the matrix comprises a synthetic or natural absorptive material, e.g., dacron, rayon, cotton or cellulose. In other embodiments the matrix comprises a synthetic or natural adsorptive material such as polystyrene, polyethylene, polypropylene or glass. A dacron or rayon tipped, plastic-shafted swab is suitable for some biological samples, e.g., those taken from the throat.

The extraction reagent may be any reagent(s), e.g., acids, bases or enzymes, suitable to successfully extract the ligand without significant degradation of the ligand or its anti-ligand(s). Nitrous acid is presently preferred for the acid extraction and Streptomyces albus enzyme is preferred for the enzymic extraction of Group A Streptococcal antigen.

Antibodies are prepared by conventional techniques. For example, antibodies can be induced by introducing the antigen into, for instance, a rabbit.

Any suitable detection method, e.g., RIA, EIA, ELISA, or FIA may be used to detect an antigen/antibody reaction product. An antibody may be labeled with radioactivity, enzymes or fluorochromes. At present, enzymes are a preferred label. Although any enzyme which can be conjugated to an antibody can be used in assays according to the present invention, peroxidases are a preferred class of enzymes and horseradish peroxidase is particularly preferred.

The chromogen for use in enzyme immunoassays according to the present invention can be any chromogen that is capable of changing or producing a color in the presence of an enzyme and its substrate. 3, 3', 5, 5'-tetramethylbenzidine (TMB) is a preferred chromogen when the enzyme used is horseradish peroxidase.

This invention is particularly suitable for the immunoassay of Group A Streptococcal antigen by (1) simultaneously carrying out the acid extraction of Group A Streptococcal antigen from a sample and reacting the antigen with at least two antibodies to form a detectable reaction product; and (2) detecting the reaction product. Although any suitable immunoassay technique, such as RIA, EIA or ELISA, may be used for the detection of Group A Streptococcal antigen, a preferred immunoassay technique is a colorimetric ELISA sandwich immunoassay wherein the first antibody is immobilized on the surface of a container and the second antibody is conjugated with an enzyme. In such colorimetric enzyme immunoassays, sufficient antigen must be extracted so that when the color formation or change occurs, the color or color change is capable of detection visually or by appropriate instrument. Quantities of Group A streptococcal antigen of $10_5$ cells and up as determined by the Breed counting technique (Modern Microbiology, Umbreit, W. W., (1962) W. H. Freeman & Co.) have been found useful in ELISA of Group A Streptococcal antigen according to the present invention. However, the method is suitable for any amount of Group A Streptococcal antigen as long as the color can be detected.

The invention also provides kits for performing the assay of a ligand extracted from a sample of cells or cell fragments, the assay comprising (1) simultaneously carrying out the extraction of the ligand from the sample and reaction of the ligand with at least two anti-ligands therefor to form a detectable reaction product; and (2) detecting the reaction product; the kit comprising, in combination: one or more solutions comprising an extraction reagent for the ligand and at least two anti-ligands capable of forming a detectable reaction product with the ligand.

In one embodiment the invention provides a kit for carrying out immunoassays, the kit comprising, in combination: one or more solutions comprising an extraction reagent for an antigen; a first antibody for the extracted antigen, the first antibody being immobilized on the surface of a container or a solid support; and a second antibody for the antigen, the second antibody being conjugated with an enzyme. In some embodiments the kit further comprises a substrate for the enzyme and a chromogen. In other embodiments, the kit further comprises an absorptive or adsorptive matrix.

The present invention also provides a method to perform an immunoassay using such kits, the method comprising: (1) absorbing in or adsorbing on a matrix, a sample containing the antigen; (2) placing the matrix, before or after absorption or adsorption of the sample, in a container, the container being coated with a substance comprising a first antibody for the antigen; (3) simultaneously carrying out the extraction of the antigen and reaction of the antigen with at least two antibodies therefor to form a detectable reaction product by (i) adding to the container one or more extraction reagents in an amount to extract at least a portion of the antigen sufficient to form a quantity of reaction product capable of detection, and a solution comprising a second antibody for the antigen, the second antibody having a detectable label, and (ii) incubating the contents of the tube for a predetermined period of time to permit extraction of the antigen from the sample and formation of the reaction product; and (4) detecting the reaction product.

The following examples are provided to further illustrate the invention.

EXAMPLE 1

Immunoassay for Acid Extracted Group A Streptococcal Antigen

In the assay described below, Group A Streptococcal antigen was simultaneously extracted from a sample of cells and captured by an immobilized antibody therefor. The assay is a solid-phase, two-site, enzyme-linked immunoassay using two polyclonal antibodies, one immobilized on a solid-phase and the other in solution and conjugated to horseradish peroxidase. The polyclonal antibodies were raised in rabbits and prepared using techniques known to those skilled in the art. The assay is a qualitative or semi-qualitative procedure.

In this assay, the sample was taken from the throat. The data was run in duplicate. Swabs containing no specimen antigen were run as negative controls and two sample swabs each containing about $10^6$ bacteria were run.

PROCEDURE

1. The specimen was collected on a dacron tipped swab. The swab was then placed into a tube coated with a first polyclonal antibody to Group A Streptococcal antigen.

Antibody: Rabbit Anti-Strep A antibody was affinity purified using N-acetyl glucosamine agarose (Sigma Chemical, St. Louis).

Antibody Coated Tubes: Polystyrene tubes (Nunc) were coated with polymerized (0.002% gluteraldedhyde) anti-strep antibody at 4 ug/tube in 250 ul of PBS with 0.1% azide overnight. The tubes were washed once with a phosphate buffer, pH 7, and incubated in a phosphate buffered saline with 4% BSA at pH 7.4 overnight. The tubes were then washed and were ready for use.

2. 105 microliters of reagent A was added to the swab, followed by 105 microliters of reagent B. Finally, 105 microliters of reagent C was added to the bottom of the tube. The reagents were constituted as follows:

Reagent A: sodium nitrite solution was made by adding 138 grams per liter sodium nitrite in distilled water.

Reagent B: acetic acid solution was made by adding 7.102 milliters of glacial acidic acid to 1 liter of distilled water.

Reagent C: conjugate solution was made by adding to one liter of distilled water, 10.46 grams per liter bis tris, 500 milliters per liter conjugate, one milliliter per liter TWEEN 20, pH 6.

Conjugate: Rabbit Anti-Strep A antibody, affinity purified, and conjugated with HRP using a modification of the Nakane method (P. K. Nakane and A. Kawasi). (J. Histochem. Cytochem. 22, 1084 (1974)).

3. These reagents were incubated for about three minutes.
4. The swab was removed and 70 microliters of wash solution was added.

Wash solution was constituted of the following: 14.09 grams per liter potassium phosphate, monobasic; 60.36 grams per liter potassium phosphate, dibasic; 8.10 grams per liter sodium chloride; 90 milliters per liter TRITON X 100, QS to one liter with distilled water, pH 7.3.

5. The tube was filled with water and decanted. This procedure was repeated with water four times.
6. The water that runs out of the tube after the last decant was blotted to prevent dilution of the next set of reagents.
7. 100 microliters of reagent D and 50 microliters of reagent E were added to the tube.

Reagent D is the substrate solution and was constituted of 13.615 grams per liter trihydrous sodium acetate, 0.47 grams per liter urea peroxide, 1.0 molar citric acid solution to pH the solution to pH 5, all dissolved in distilled water.

Reagent E is a chromogen solution and was made by adding 500 milliters of methanol to 500 milliters of glycerol and adding 1.27 grams of TMB to that one liter of solution. TMB is 3, 3', 5, 5' tetramethylbenzidine.

8. The tube was incubated for three minutes.
9. To determine the optical density (O.D.), the tubes were then filled with a one milliter 0.5N sulfuric acid solution, the O.D. read in an analyzer at 450 nanometers.

| TUBE | O.D. |
|---|---|
| CONTROL 1 | 0.041 |
| CONTROL 2 | 0.040 |
| SAMPLE 1 | 0.463 |
| SAMPLE 2 | 0.228 |

The presence of a blue color of greater intensity than the negative control was considered a positive result. Variations of sample O.D. were encountered due to variations in absorption of the reagents in the swab.

EXAMPLE 2

Determination of Optimum pH for Acid Extraction and Immunochemical Binding of Group A Streptococcal antigen A. Acid Extraction Immunoassays were carried out to determine the optimum pH for the extraction of Group A Streptococcal antigen as described in Example I above, except that Group A Streptococcal antigen was extracted at several different pH values. The results of this assay are shown in FIG. 1.

B. Immunochemical Binding

Immunoassays to determine the optimum pH for immunochemical binding of Group A Streptococcal antigen were carried out as described in Example I above except that nitrous acid extracted Streptococci were used as the sample and the assays were conducted at several different pH values. The results of this assay are shown in FIG. 1.

C. Results

The optimum pH for carrying out the simultaneous extraction and immunochemical binding of Group A Streptococcal antigen according to the immunoassay assay of Example I above was determined to be about pH 4.4.

EXAMPLE 3

Immunoassay for Group A Streptococcal Antigen

The assay described below is a quantitative solid-phase, two-site enzyme-linked immunoassay using two polyclonal antibodies, one immobilized on a solid-phase and the other in solution and conjugated to horseradish peroxidase. This assay is carried out using antibodies, antibody coated tubes, conjugate, substrate, chromogen and wash solution prepared as described in Example I, above.

1. A measured aliquot, between 10 to 30 microliters, of a sample containing a suspension of Streptococci A is added to a tube coated with a first polyclonal antibody.
2. 105 microliters of reagent A is added to the tube, followed by 105 microliters of reagent B. Finally, 105 microliters of reagent C is added to the bottom of the tube.
3. These reagents are incubated for about three minutes.
4. 70 microliters of wash solution is added.
5. The tube is filled with water and decanted and this procedure is repeated with water four times.
6. The water that runs out of the tube after the last decant is blotted to prevent dilution of the next set of reagents.
7. 100 microliters of reagent D and 50 microliters of reagent E is added to the tube.
8. The tube is incubated for about two minutes or longer.
9. Samples are run in duplicate. Standard curves are run to determine the number of bacteria per ml per O.D. unit. A standard Streptococci suspension is obtained by determining the number of bacteria per milliliter using standard colony count methodology. Aliquots of the standard suspension and the sample are assayed following the same procedure, including incubation times.

EXAMPLE 4

Immunoassay for Enzyme Extracted Group A Streptococcal Antigen

This assay was carried out using antibodies, antibody coated tubes, conjugate, substrate and chromogen prepared as described in Example I, above. Streptomyces albus enzyme was used to extract Group A Streptococcal antigen in this assay.

Procedure:

(1) An overnight broth culture of Streptococcus Group A culture was centrifuged and resuspended in phosphate buffered saline to an O.D. of 0.03 as measured in a Coleman spectrophotometer at 630 nm. This suspension represents $5 \times 10^7$ cells/ml as determined by colony count or the Breed Method (supra). 20 microliters of this suspension was added to an anti-Strep A antibody coated tube. Streptomyces Albus Enzyme: Streptomyces albus enzyme was made following the procedure of W. R. Maxted. *The Lancet*, Vol. 2, Aug. 14, 1948, pp. 255-256.

(2) 50 ul of the conjugate containing 0.1% Tween 20 was added to the tube.

(3) 300 ul of the Streptomyces albus enzyme was added to the tube.

(4) The solution of step 3 was incubated for 20 minutes at room temperature.

(5) The tube was washed 5 times with tap water.

(6) 100 ul of substrate and 50 ul of chromogen were added to the tube and incubated for 5 min. at room temperature.

(7) 1 ml. of 0.5 $NH_2SO_4$ tube was added and the tubes read in a spectrophotometer at 450 nm.

| RESULTS | |
|---|---|
| Antigen Concentration (# bacteria/tube) | O.D. |
| 0 | 0.032 |
| 0 | 0.040 |
| $1 \times 10^6$ | 0.332 |
| $1 \times 10^6$ | 0.357 |

The examples described above using a solid-phase, two-site enzyme-linked simultaneous immunoassay are merely two examples of the use of the present invention. Variations in the actual process described in the examples will be apparent to those skilled in the art. Therefore, the present invention is to be considered limited only by the appended claims.

What is claimed is:

1. A method for performing the assay of a ligand extracted from a sample of cells or cell fragments, the method comprising: (1) simultaneously carrying out the extraction of the ligand from the sample and reaction of the ligand with at least two anti-ligands therefor to form a detectable reaction product; and (2) detecting the reaction product.

2. The method of claim 1 wherein the sample is absorbed in or adsorbed on a matrix.

3. The method of claim 2 wherein the matrix comprises at least one synthetic or natural, absorptive or adsorptive material.

4. The method of claim 2 wherein the matrix is polystyrene, polyethene, polypropylene, nylon, dacron, rayon, cotton or cellulose.

5. The method of claim 1 wherein the extraction step comprises, extracting the sample with one or more extraction reagents in an amount to extract at least a portion of the ligand sufficient to form a quantity of reaction product capable of detection.

6. The method of claim 1 wherein at least one anti-ligand is immobilized on a solid support.

7. The method of claim 1 wherein a first anti-ligand is immobilized on a solid support and a second anti-ligand is labeled with a detectable label.

8. The method of claim 7 wherein the label is a radioactive, fluorochrome or enzyme label.

9. The method of claim 8 wherein the ligand is an antigen, the first and second anti-ligands are antibodies and the detectable label is an enzyme.

10. The method of claim 9 wherein the enzyme is a peroxidase.

11. The method of claim 10 wherein the peroxidase is horseradish peroxidase.

12. The method of claim 9 wherein the reaction product is detected by a colorimetric reaction of the enzyme with a substrate for the enzyme and a chromogen.

13. The method of claim 12 wherein the chromogen is a tetramethylbenzidine.

14. The method of claim 1 wherein the cells or cell fragments are microbial or mammalian cells or cell fragments.

15. The method of claim 1 wherein the ligand is Group A Streptococcal antigen and the extraction reagent comprises nitrous acid or Streptomyces albus enzyme.

16. A method for performing an immunoassay of an antigen extracted from a sample of cells or cell fragments, the method comprising: (1) absorbing in or adsorbing on a matrix the sample containing the antigen; (2) placing the matrix, before or after absorption or adsorption of the sample, in a container, the container being coated with or containing an immobilized substance comprising a first antibody for the antigen; (3) simultaneously carrying out the extraction of the antigen and reaction of the antigen with at least two antibodies therefor to form a detectable reaction product by (i) adding to the container one or more extraction reagents in an amount to extract at least a portion of the antigen sufficient to form a quantity of reaction product capable of detection and a solution comprising a second antibody for the antigen, the second antibody having a detectable label, and (ii) incubating the contents of the tube for a predetermined period of time to permit extraction of the antigen from the sample and formation of the detectable reaction product; and (4) detecting the reaction product.

17. The method of claim 16 wherein the matrix comprises at least one synthetic or natural, absorptive or adsorptive material.

18. The method of claim 17 wherein the matrix is polystyrene, polyethylene, polypropylene, nylon, dacron rayon, cotton or cellulose.

19. The method of claim 16 wherein the cells or cell fragments are microbial or mammalian cells or cell fragments.

20. The method of claim 16 wherein the antigen is Group A Streptococcal antigen and the extraction reagent comprises nitrous acid or Streptomyces albus enzyme.

21. The method of claim 16 wherein the detectable label is a radioactive, fluorochrome or enzyme label.

22. The method of claim 21 wherein the enzyme is a peroxidase.

23. The method of claim 22 wherein the peroxidase is horseradish peroxidase.

24. The method of claim 16 wherein the detection step comprises: washing the container; adding to the container a substrate for the enzyme and a chromogen; and detecting a color change or formation, visually or instrumentally.

25. The method of claim 24 wherein the substrate is a peroxide.

26. The method of claim 25 wherein the peroxide is hydrogen peroxide.

27. The method of claim 24 wherein the chromogen is a tetramethylbenzidine.

28. The method of claim 16 wherein the extraction reagent is essentially absorbed in the matrix; a solution comprising the second antibody is added to the bottom of the container; and the contents of the container is incubated for a period of time to enable the antigen to diffuse from the matrix into the second antibody solution and to form the reaction product.

* * * * *